(12) United States Patent
Mitchell et al.

(10) Patent No.: US 7,882,970 B2
(45) Date of Patent: Feb. 8, 2011

(54) ANESTHETIC CONTAINER

(75) Inventors: Nathan Mitchell, Volo, IL (US); Robert Gliniecki, Spring Grove, IL (US)

(73) Assignees: Baxter Healthcare Corporation, Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 277 days.

(21) Appl. No.: 12/166,986

(22) Filed: Jul. 2, 2008

(65) Prior Publication Data
US 2010/0000958 A1 Jan. 7, 2010

(51) Int. Cl.
*B65D 41/00* (2006.01)
*B65D 1/02* (2006.01)
*B65D 51/16* (2006.01)

(52) U.S. Cl. .................. 215/45; 215/40; 215/902; 220/366.1; 220/367.1

(58) Field of Classification Search ................ 215/11.4, 215/11.5, 40, 45, 902; 220/366.1, 367.1
See application file for complete search history.

(56) References Cited

U.S. PATENT DOCUMENTS

| | | | |
|---|---|---|---|
| 2,340,024 A * | 1/1944 | Skaller ........................ 206/440 |
| 5,144,991 A | 9/1992 | Wallroth et al. |
| 5,287,898 A | 2/1994 | Falb et al. |
| 5,381,836 A | 1/1995 | Braatz et al. |
| 5,427,145 A | 6/1995 | Grabenkort |
| 5,465,864 A | 11/1995 | McClean |
| 5,474,112 A | 12/1995 | Carola |
| 5,505,236 A | 4/1996 | Grabenkort et al. |
| 5,617,906 A | 4/1997 | Braatz et al. |
| 5,682,874 A | 11/1997 | Grabenkort et al. |
| 5,727,715 A * | 3/1998 | McKenna et al. ...... 222/189.09 |
| 5,758,640 A | 6/1998 | Kamppari et al. |
| 5,810,001 A | 9/1998 | Genga et al. |
| 5,915,427 A | 6/1999 | Grabenkort |
| 5,927,559 A | 7/1999 | Bommer et al. |

(Continued)

FOREIGN PATENT DOCUMENTS

WO    WO 94/15656    7/1994

(Continued)

OTHER PUBLICATIONS

International Search Report and Written Opinion for counterpart International Application No. PCT/US2009/048438, Oct. 12, 2009 (9 pages).

*Primary Examiner*—Anthony Stashick
*Assistant Examiner*—Madison L Wright
(74) *Attorney, Agent, or Firm*—Marshall, Gerstein & Borun LLP

(57) ABSTRACT

An anesthetic container includes a bottle having a wall defining a receptacle and a neck with a passage in fluid communication with the receptacle, a valve assembly including a flange, and a ferrule disposed over at least a portion of the flange of the valve assembly and about at least a portion of the neck of the bottle to secure the valve assembly to the bottle. One of the wall of the bottle, the flange of the valve assembly or a wall of the ferrule has at least one vent formed, at least in part, therein that permits air trapped between the ferrule and the valve assembly or the bottle to escape.

28 Claims, 4 Drawing Sheets

U.S. PATENT DOCUMENTS

| | | |
|---|---|---|
| 6,125,893 A | 10/2000 | Braatz et al. |
| 6,341,706 B1 * | 1/2002 | Neuner .................... 215/40 |
| 6,394,087 B1 | 5/2002 | Kankkunen et al. |
| 6,585,016 B1 | 7/2003 | Falligant et al. |
| 6,817,390 B2 | 11/2004 | Falligant et al. |
| 6,929,041 B2 | 8/2005 | Falligant et al. |
| 7,040,511 B1 | 5/2006 | Petit |

FOREIGN PATENT DOCUMENTS

| | | |
|---|---|---|
| WO | WO 98/25665 | 6/1998 |

* cited by examiner

ANESTHETIC CONTAINER

BACKGROUND

This patent is directed to an anesthetic container, and, in particular, to an anesthetic container with a quality control improvement.

Many forms of anesthetic are stored as a liquid for later use in their vapor state. The liquid form is more compact for storage, and can be converted through the use of a vaporizer, where the liquid form is allowed to convert into its vapor state in a controlled environment. Typically, the storage device is a container including a bottle with an opening that has been occluded through the use of a cap and/or a valve.

It will be recognized that the cooperation between the valve and the bottle is of significant importance in maintaining the liquid anesthetic in the container. If the cap or valve and the bottle do not have a fluid-tight seal (whether that fluid be a liquid or a vapor), the liquid anesthetic may escape from the container. This situation is to be avoided because the escaping product may represent a potential hazard for those persons in the immediate area around a leaking container. Moreover, if the anesthetic is leaking from the container, it may not be possible to accurately determine the amount of anesthetic remaining in the bottle, leading to other issues. Lastly, the leakage of product from the container may represent a financial loss.

To limit the possibility that a leaking container will be distributed, testing is typically performed at the facility where the containers are filled. In particular, a vacuum test may be performed on each container before it leaves the facility. According to the conventional vacuum test protocol, a container is placed in a chamber, and the air in the chamber is evacuated to approximately 8 pounds per square inch (psi) in approximately 6 seconds. The system is then permitted to stabilize for 2-3 seconds. After the stabilization period, the pressure in the chamber is measured for 6 seconds, and any vacuum decay within the chamber is taken as an indication that gas from the bottle has escaped into the chamber, resulting in a pressure rise within the chamber.

It has been determined, however, that this testing method results in significant a number of false rejects. A false reject occurs when the vacuum test suggests that a container is leaking when, in actuality, the container is fluid-tight. The rate of identification of false rejects may be in excess of 300% when viewed on a relative basis to the number of actual rejects (i.e., containers that actually are not fluid-tight). Still, the vacuum test remains a widely used test, given its simplicity which permits its use with the significant numbers of containers that are filled on a daily basis.

As set forth in more detail below, the present disclosure sets forth an improved assembly embodying advantageous alternatives to the conventional devices and methods discussed above.

SUMMARY OF THE INVENTION

In one aspect, an anesthetic container includes a bottle having a wall defining a receptacle and a neck with a passage in fluid communication with the receptacle, a valve assembly including a flange, and a ferrule disposed over at least a portion of the flange of the valve assembly and about at least a portion of the neck of the bottle to secure the valve assembly to the bottle. The ferrule has at least one vent formed in a wall of the ferrule that permits air trapped between the ferrule and the valve assembly or the bottle to escape.

In another aspect, an anesthetic container includes a bottle having a wall defining a receptacle and a neck with a passage in fluid communication with the receptacle, a valve assembly including a flange, and a ferrule disposed over at least a portion of the flange of the valve assembly and about at least a portion of the neck of the bottle to secure the valve assembly to the bottle. The valve assembly has at least one vent formed, at least in part, in the flange that permits air trapped between the ferrule and the valve assembly or the bottle to escape.

In a further aspect, an anesthetic container includes a bottle having a wall defining a receptacle and a neck with a passage in fluid communication with the receptacle, a valve assembly including a flange, and a ferrule disposed over at least a portion of the flange of the valve assembly and about at least a portion of the neck of the bottle to secure the valve assembly to the bottle. The bottle has at least one vent formed, at least in part, in the wall of the bottle that permits air trapped between the ferrule and the valve assembly or the bottle to escape.

Additional aspects of the disclosure are defined by the claims of this patent.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF VARIOUS EMBODIMENTS

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

Figure 1:
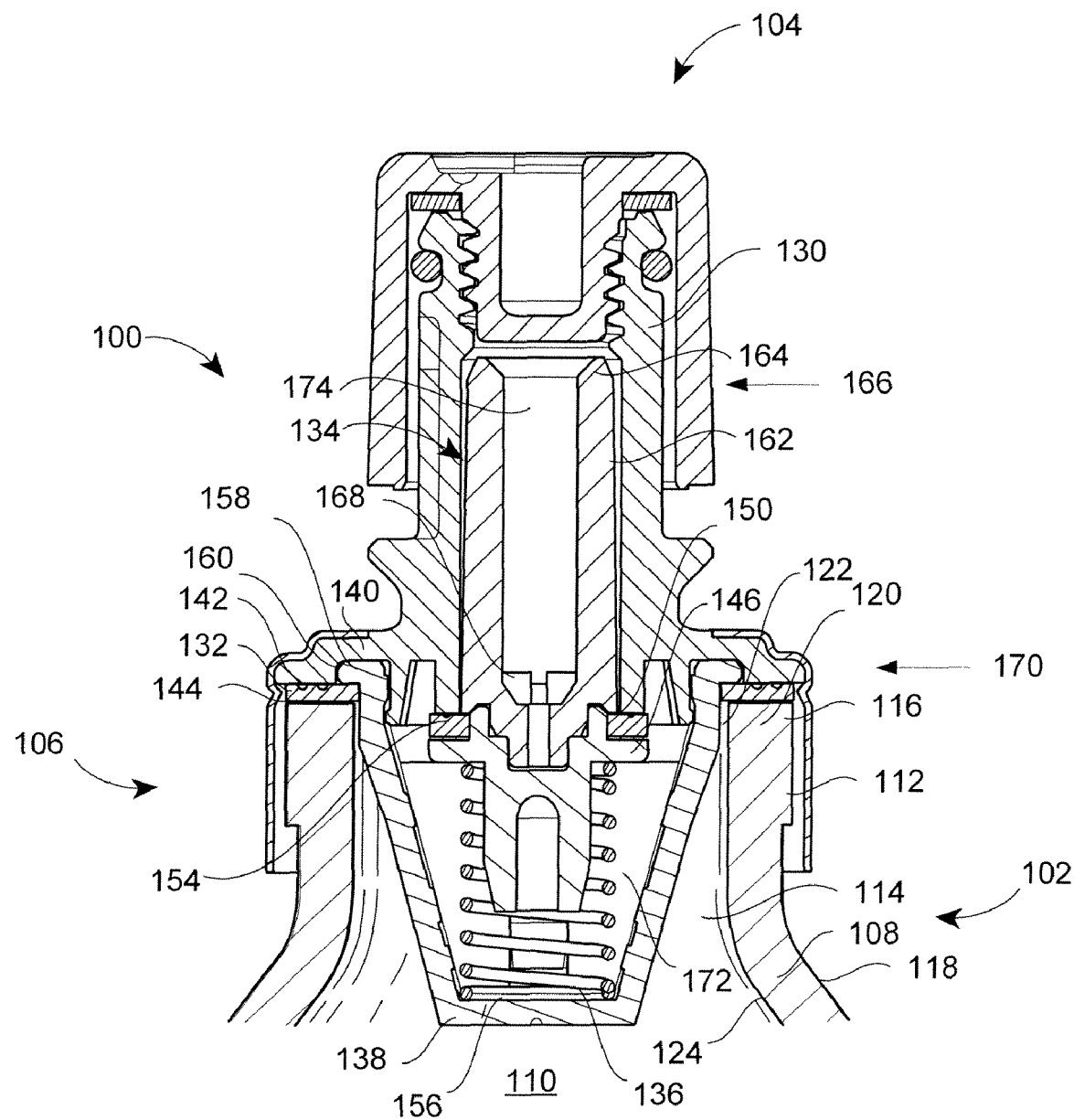
FIG. 1 is a cross-sectional view of a container according to the present disclosure.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph FIG. 1 illustrates an embodiment of an anesthetic container 100. The container 100 includes a bottle 102, a valve assembly 104, and a ferrule 106. The container 100 may also include a cap that is fitted over the end of the valve assembly 104, providing a barrier to anesthetic loss as well as limiting access to and contamination of the valve assembly 104.

Figure 2:
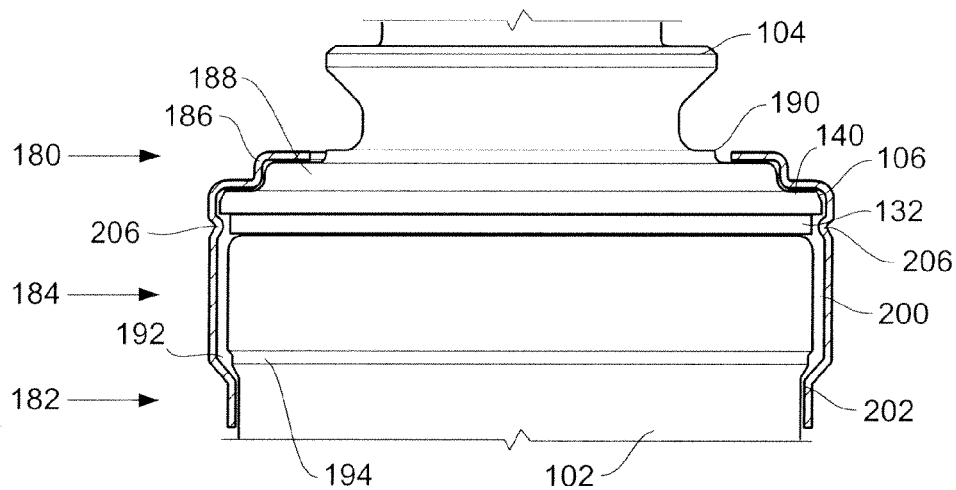
FIG. 2 is a partial cross-section of a container according to the present disclosure, exposing the interface between the bottle, valve assembly and ferrule.

The bottle 102 has a wall 108 that defines a receptacle 110 and a neck 112 with a passage 114 in fluid communication with the receptacle 110. As illustrated in FIGS. 1 and 2, the embodiment of the bottle 102 has a neck 112 with a smaller cross-section than the receptacle 110; this need not be the case according to all embodiments of the present disclosure. In addition, the bottle 102 has a flange 116, preferably positioned at the neck 112 of the bottle. As illustrated in FIG. 1, the flange 116 may depend from an outer surface 118 of the wall 108 to define a rim 120 about an opening 122 in communication with the passage 114 through the neck 112.

Figure 3:
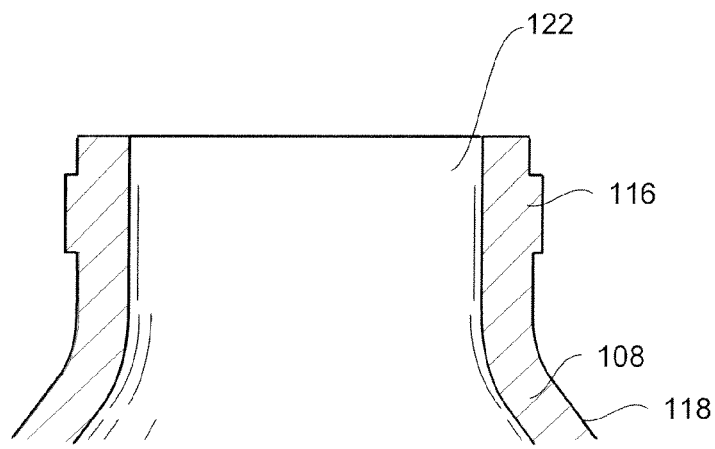
FIG. 3 is another embodiment of a bottle for use in the container according to the present disclosure.
Figure 4:
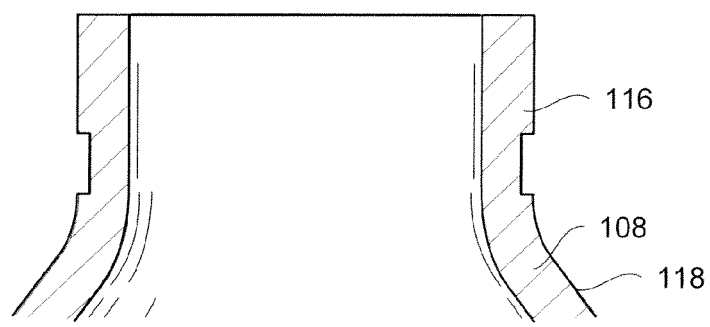
FIG. 4 is a further embodiment of a bottle for use in the container according to the present disclosure.

It will be recognized that this is only one embodiment, and that the flange may, for example, be disposed at other locations on or along the bottle 102. As one alternative, the flange 116 maybe spaced from the opening 122, as shown in FIG. 3. As a further alternative, the flange 116 may be defined not by a projection depending from the outer surface 118 of the wall 108, but by a depression depending into the outer surface 118 of the wall 108, as shown in FIG. 4. Other alternatives are also possible.

According to an embodiment of the present disclosure, the bottle 102 is made of glass. According to other embodiments, the bottle 102 may be made of metal, for example, aluminum; according to still other embodiments, the bottle 102 may be made of a polymer, such as polyethylene terephthalate (PET). Furthermore, according certain embodiments, a polymer or other material may be applied as a thin layer to the outer surface 118 of the wall 108. Additionally, according to further embodiments, a polymer or other material may be applied as a thin layer to an inner surface 124 of the wall 108.

The valve assembly 104 is attached to the bottle 102 to control passage of fluids in and out of the bottle 102. The valve assembly 104, as illustrated in FIGS. 1 and 2, includes a conduit 130, a gasket 132, a valve member 134, a resilient member 136 and a cage 138.

The valve assembly 104 includes a flange 140. In the embodiment illustrated, the flange 140 formed integrally with the conduit 130. The flange 140 cooperates with the rim 120 disposed about the opening 122. As illustrated, the flange 140 has a surface 142 that faces a surface 144 of the flange 116 of the bottle 102. Disposed between these surfaces 142, 144 is the gasket 132, which may be made of an elastomeric material. The gasket 132 assists in forming a fluid-tight connection between the surfaces 142, 144 when the surfaces 142, 144 are assembled as illustrated.

The valve member 134 particularly functions to control passage of fluids through the conduit 130. In particular, the valve member 134 includes a plate 146 at a first end of the valve member 134. In the closed position illustrated, the plate 146 occludes an opening 150 at a first end of the conduit 130 to limit passage of fluids therethrough; according to certain embodiments, the plate 146 forms a fluid-tight seal with a gasket 154 disposed about the opening 150 of the conduit 130.

The valve member 134 is biased towards a closed position, illustrated in FIG. 1, through the action of the resilient member 136, which may be a spring, as illustrated. In particular, the resilient member 136 is disposed between the plate 146 of the valve member 134 and a surface 156 of the cage 138. The cage 138 is held in place through the cooperation of a rim 158 of the cage 138 and the conduit 130, the gasket 132, and the rim 120 of the bottle 102. Particularly, the rim 158 of the cage 138 is disposed between a shoulder 160 formed in the flange 140, the gasket 132, and the rim 120 of the bottle 102.

The valve member 134 may include structures or partitions that guide the flow of more than one fluid at a time. In particular, the valve member 134 may include a tube 162, having an opening 164 at a first end 166 and at least one opening 168 at a second end 170; as illustrated, a plurality of openings 168 are provided in the second end 170. While the tube 162 is illustrated as coaxial with the conduit 130, this need not be the case according to all embodiments of the present disclosure.

In operation, when the valve member 134 is biased away from the closed position, liquid anesthetic is permitted to flow through openings 172 in the cage 138, the opening 150 in the conduit 130, and a passage defined between the tube 162 and the conduit 130 into an associated vaporizer. At the same time, the first end 166 of the tube 162 is in fluid communication with a portion of the vaporizer through which vapor returns to the bottle 102. This vapor passes through the opening 164 in the first end 166 of the tube 162, through a passage 174 defined through the tube 162, out of the at least one opening 168 in the second end 170 of the tube 162, and into the bottle 102.

It will be recognized that while an embodiment of the valve assembly 104 has been illustrated herein, the present disclosure is not limited to only such an arrangement. For example, the structure and operation of the valve assembly 104 may differ, as may the cooperation between the flange 140 of the conduit 130, the gasket 132, the cage 138, and the rim 120 of the bottle 102. Structures shown as separate elements may be joined or formed together, and structures illustrated as formed integrally (i.e., as one piece) may be formed as separate elements.

As noted above, as assembled, the surface 142 of the flange 140 of the conduit 130 faces the surface 144 of the flange 116 of the bottle 102, with various other structures, such as the gasket 132 and a portion of the cage 138, optionally disposed therebetween. To secure the valve assembly 104 and the bottle 102 with the elements so disposed, the ferrule 106 is disposed over and about elements of the valve assembly 104 and the bottle 102, and then preferably secured to the valve assembly 104 and to the bottle 102. As illustrated, the ferrule 106 is deformed over at least a portion of the flange 140 and about at least a portion of the neck 112 (and preferably about, the flange 116) of the bottle 102, through a mechanical process, such as crimping. It will be recognized, however, that other joining methods may also be used to secure the bottle 102, the valve assembly 104, and the ferrule 106.

Figure 6:
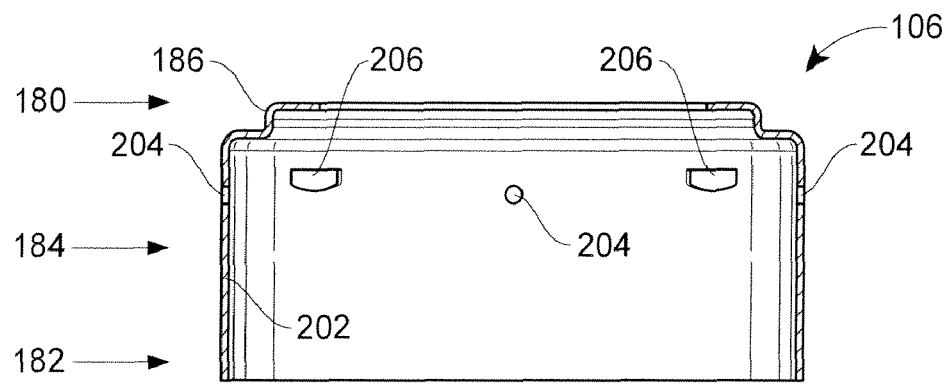
FIG. 6 is a cross-sectional view of a ferrule according to the present disclosure taken along line 6-6 in FIG. 5.

Specifically, the ferrule 106 may be disposed about the neck 112 of the bottle 102 and over and about the flange 140 of the conduit 130 to secure the conduit 130, and thus the valve assembly 104, to the bottle 102. In particular, as best seen in FIG. 2, the ferrule 106 has a first end 180 through which at least a portion of the valve assembly 104 depends, a second end 182 through which the bottle 102 depends, and a central region 184 between the first end 180 and the second end 182. The first end 180 may have one or more shoulders 186 that are designed to cooperate with one or more shoulders 188 formed on a surface 190 of the flange 140 of the valve assembly 104 (and thus of the conduit 130 which includes the flange 140). The second end 182 is generally cylindrical prior to assembly (as shown in FIGS. 1 and 6, for example), and is forced inward during the crimping process such that an inner surface 192 of the ferrule 106, in particular in portion of the inner surface 192 at the second end 182 of the ferrule 106, cooperates with a shoulder 194 defined by the flange 116 of the bottle 102 (as shown in FIG. 2, for example) to secure the valve assembly 104 to the bottle 102.

As best seen in FIG. 2, when the ferrule 106 is crimped over the flange 116 of the bottle 102, a space 200 is formed between the outer surface 118 of the wall 108 of the bottle 102 and the inner surface 192 of the ferrule 106, which is also the inner surface of a wall 202 of the ferrule 106. The space 200 may also exist between the inner surface 192 of the ferrule 106 and the outer surface 190 of the conduit 130 (in particular, the flange 140) and of the gasket 132. It is presently believed that air may become entrapped in this space 200 during the crimping process.

While the crimping process is sufficient to force the second end 182 of the ferrule 106 about the flange 116, it is insufficient to form a fluid-tight seal along the interface between the ferrule 106 and the flange 116, or between the shoulders 186, 188 of the ferrule 106 and the valve assembly 104. As a consequence, air is able to pass through the gaps between the ferrule 106 and the flange 116 and/or between the ferrule 106 and the valve assembly 104 into the surrounding environment. While this is not generally problem, the slow escape of air from the space during the vacuum leak test described above can lead to a vacuum decay reading that would normally be suggestive of a leak in the container 100. The ultimate result is a false reject of a container that is otherwise fluid-tight.

To prevent the slow leakage of trapped air in the space 200, which may lead to false rejects, it has been determined that at least one vent 204 should be formed in the wall 202 of the ferrule 106 to permit air trapped between the ferrule 106 and the valve assembly 104 or the bottle 102 to escape quickly during the evacuation of the test chamber in the vacuum leak test described above. See FIGS. 5 and 6. It is presently believed that by venting the air quickly, the number of false rejects may be reduced. The vents 204, which are apertures or holes that extend through the wall 202 of the ferrule 106, should not be confused with undercuts 206, which are not in fact holes or apertures, as may be seen in FIG. 2.

It will be readily appreciated that while an embodiment of vents 204 according to the present disclosure has been illustrated, this exemplary embodiment is not intended to be limiting on the invention thus embodied. However, the present embodiment may be helpful in illustrating one or more aspects which may be present in a container 100 according to the present disclosure.

Figure 5:
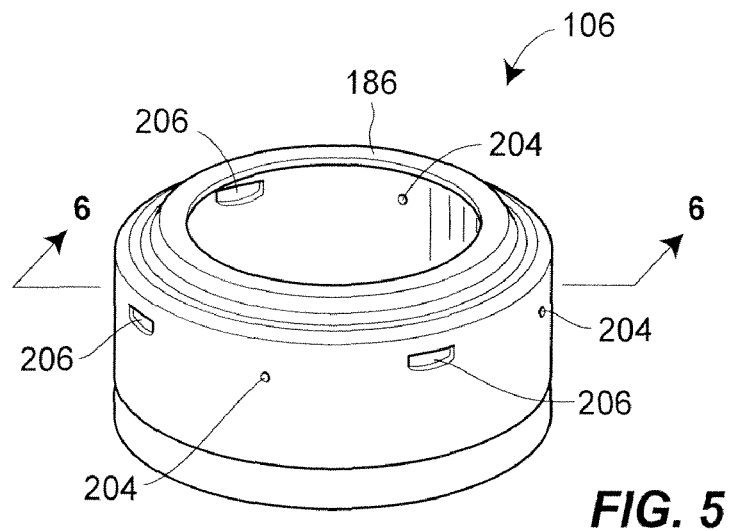
FIG. 5 is a perspective view of a ferrule according to the present disclosure.

Initially, as illustrated best in FIGS. 5 and 6, the at least one vent 204 may be a plurality of vents 204, which vents 204 are disposed about the periphery of the ferrule 106. In particular, four vents 204 have been disposed about the ferrule 106. As illustrated, the vents 204 are equally spaced about the periphery of the ferrule 106. The vents 204 are also disposed approximately equidistant from the undercuts 206. However, it will be appreciated that this is only one arrangement of the vents 204; other embodiments may include a greater or lesser number of vents 204, may vary the spacing between vents 204, and may vary the spacing between the vents 204 and the undercuts 206.

It will also be recognized that the vents 204 are formed in the central region 184 of the ferrule 106, and in particular closer to the first end 180 of the ferrule 106 than the second end 182 of the ferrule 106. While the placement of the vent 204 is not so limited in all embodiments, it is believed that the illustrated placement of the vents 204 is advantageous. Specifically, it will be noted that the distance is greatest between the inner surface 192 of the ferrule 106 and the outer surface of the assembly of the conduit 130, gasket 132 and bottle 102 where the flange 116 of the bottle 102 interfaces with the gasket 132 along the surface 142 because of a slight radius at this point. By aligning the vents 204 with the point of greatest distance between the facing surfaces, the possibilities of occlusion of the vents 204 by, for example, the bottle 102, may be reduced. It will be recognized that the placement of vents 204 at different points about the periphery of the ferrule 106 also reduces the possibilities that either the conduit 130, gasket 132 or bottle 102 will occlude all of the vents 204, thus permitting at least one of the vents 204 to be available to allow the trapped air to escape.

As illustrated, the vent 204 is formed as a circular hole in the wall 202 of the ferrule 106. Here again, it is not critical to the present disclosure that the vent be a circular hole; other shapes may be used as well. Moreover, it is not intended that the relative size of the vent 204, as illustrated, be intended to understood to limit the vent 204 to only such a size; it is possible that the vent 204 be larger or smaller than that shown on a relative or an absolute basis.

It will also be recognized that while the vents 204 are formed in the wall 202 of the ferrule 106 in the embodiment shown, it is also possible for the vents to be formed in or defined by other elements of the container 100 as well. Four such additional embodiments are illustrated in FIGS. 7-10, with structures similar to those of the embodiments illustrated in FIGS. 1-6 numbered similarly.

Figure 7:
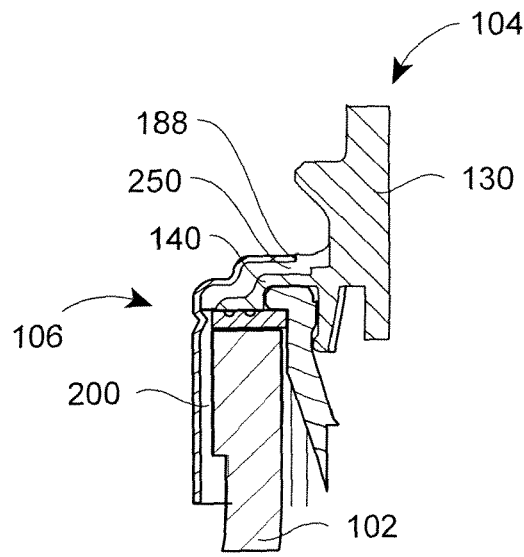
FIG. 7 is a partial cross-sectional view of an embodiment of an alternative combination of ferrule and valve assembly according to the present disclosure.
Figure 8:
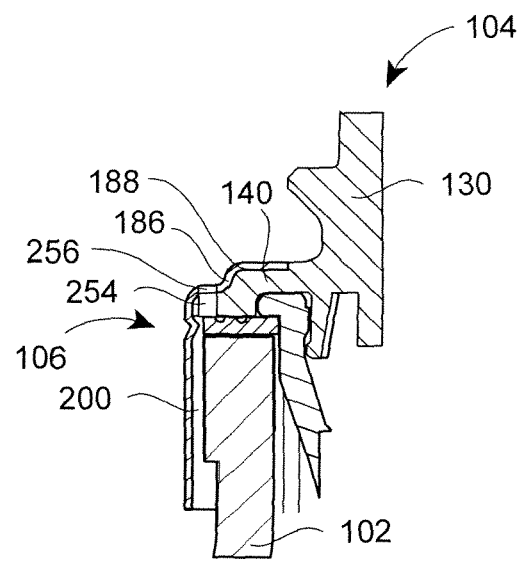
FIG. 8 is a partial cross-sectional view of an embodiment of another alternative combination of ferrule and valve assembly according to the present disclosure.

FIGS. 7 and 8 illustrate embodiments wherein passages in a portion of the valve assembly define, in whole or in part, vents to permit the escape of air from the space 200. In particular, in the embodiments of FIGS. 7 and 8, the flange 140 of the valve assembly 104, which flange 140 may be formed integrally with the conduit 130, includes one or more passages which may, in whole or in part, define vents similar to those described above. While one passage is shown in FIGS. 7 and 8, it will be recognized that the passages may be spaced about the flange 140 in the same manner in which the vents 204 are disposed about the ferrule 106 in FIGS. 3 and 4. According to the embodiment illustrated in FIG. 7, the one or more passages 250, each of which may be in the form of a groove, may extend up the shoulder 188 of the flange 140 under the ferrule 106. According to the embodiment illustrated in FIG. 8, the flange 140 may have one or more passages 254, and the ferrule 106 may have one or more apertures 256 formed in the shoulder 186 to expose the passages 254. According to still other embodiments similar to that illustrated in FIG. 8, the apertures 256 may have one or more surfaces that cooperate with the passages 254 to align the apertures 256 with the passages 254.

Figure 9:
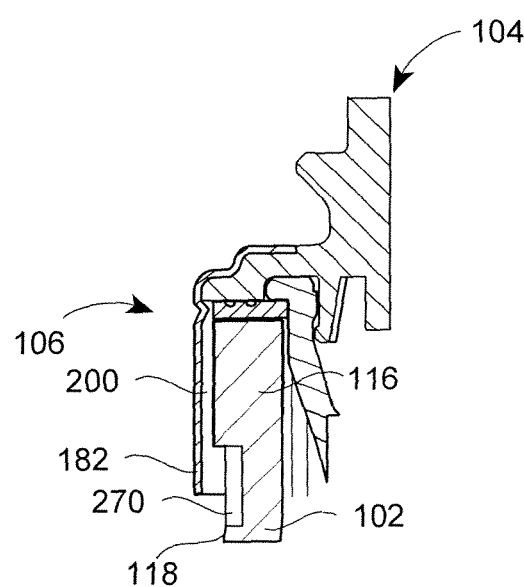
FIG. 9 is a partial cross-sectional view of an embodiment of an alternative combination of ferrule and bottle according to the present disclosure.
Figure 10:
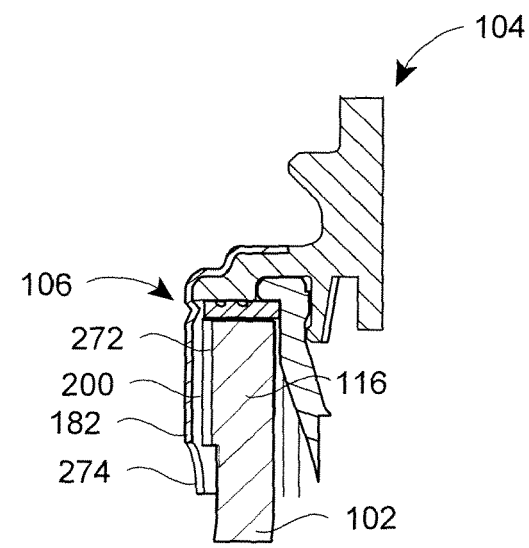
FIG. 10 is a partial cross-sectional view of an embodiment of another alternative combination of ferrule and bottle according to the present disclosure.

As seen in FIGS. 9 and 10, it is also possible that the bottle 102 may be formed in such a manner that the vent is defined in the bottle 102, such that when the end 182 of the ferrule 106 is crimped about the flange 116, the vent provides open access to the external environment. According to the embodiment of FIG. 9, one or more passages 270 may be formed below the flange 116; while one passage 270 is shown in FIG. 9, it will be recognized that a series of spaced passages 270 may be spaced about the bottle 102. The distance across the passage 270, which may be defined by a groove in the exterior surface 118 of the bottle 102, may be selected to inhibit crimping of the ferrule 106 into the groove 270, thereby maintaining open access to the space 200. FIG. 10 illustrates an alternative embodiment wherein the passages 272, which may be in form of grooves, are formed in the flange 116, and the ferrule 106 includes apertures 274 to expose the passages 272 when the ferrule 106 is crimped about the flange 116.

We claim:

1. An anesthetic container comprising:
    a bottle having a wall defining a receptacle and a neck with a passage in fluid communication with the receptacle;
    a valve assembly including a flange with a fluid-tight connection to the bottle; and
    a ferrule disposed over at least a portion of the flange of the valve assembly and about at least a portion of the neck of the bottle to secure the valve assembly to the bottle and to form a space between the ferrule and the valve assembly or bottle,
    the ferrule having at least one vent formed in a wall of the ferrule that permits air trapped in the space between the ferrule and the valve assembly or the bottle to escape.

2. The container according to claim 1, wherein the at least one vent comprises a plurality of vents disposed about a periphery of the ferrule.

3. The container according to claim 2, wherein the vents are equally spaced about the periphery of the ferrule.

4. The container according to claim 1, wherein;
    the ferrule comprises a first end through which at least a portion of the valve assembly depends, a second end through which the bottle depends, and a central region between the first end and the second end; and
    the at least one vent is formed in the central region of the ferrule.

5. The container according to claim 4, wherein the at least one vent is disposed closer to the first end of the ferrule than the second end of the ferrule.

6. The container according to claim 1, wherein the vent comprises a circular hole in the wall of the ferrule.

7. The container according to claim 1, wherein the bottle includes a flange, the ferrule being formed about the flange of the valve assembly and the flange of the bottle.

8. The container according to claim 7, wherein the flange of the bottle is positioned at the neck of the bottle.

9. The container according to claim 7, further comprising a gasket disposed between the flange of the valve assembly and the flange of the bottle.

10. The container according to claim 9, wherein the at least one vent is aligned with an interface between the gasket and the flange of the bottle.

11. The container according to claim 1, wherein the valve assembly comprises a conduit, the flange of the valve assembly being formed integrally with the conduit.

12. The container according to claim 11, wherein the conduit has an opening, and the valve assembly comprises a moveable valve member that occludes the opening in a closed position to limit passage of fluids through the opening.

13. The container according to claim 12, wherein the valve member is biased towards the closed position by a resilient member.

14. The container according to claim 1, wherein the wall of the bottle comprises glass.

15. The container according to claim 14, wherein the wall of the bottle has an outer surface, the outer surface having a polymer layer applied thereto.

16. The container according to claim 1, wherein the wall of the bottle comprises metal.

17. The container according to claim 16, wherein the wall of the bottle comprises aluminum.

18. The container according to claim 16, wherein the wall of the bottle has an outer surface, the outer surface having a polymer layer applied thereto.

19. The container according to claim 16, wherein the wall of the bottle has an inner surface, the inner surface having a polymer layer applied thereto.

20. An anesthetic container comprising:
    a bottle having a wall defining a receptacle and a neck with a passage in fluid communication with the receptacle;
    a valve assembly including a flange, a conduit, the flange of the valve assembly being formed integrally with the conduit and the conduit having an opening, a moveable valve member that occludes the opening in a closed position to limit passage of fluids through the opening, and a tube disposed within the conduit, defining a first passage through the tube and a second passage between the tube and the conduit; and
    a ferrule disposed over at least a portion of the flange of the valve assembly and about at least a portion of the neck of the bottle to secure the valve assembly to the bottle,
    the ferrule having at least one vent formed in a wall of the ferrule that permits air trapped between the ferrule and the valve assembly or the bottle to escape.

21. The container according to claim 20, wherein the bottle includes a flange positioned at the neck of the bottle, the ferrule being formed about the flange of the valve assembly and the flange of the bottle.

22. The container according to claim 20, wherein the bottle includes a flange, the ferrule being formed about the flange of the valve assembly and the flange of the bottle, and further comprising a gasket disposed between the flange of the valve assembly and the flange of the bottle.

23. The container according to claim 22, wherein the at least one vent is aligned with the interface between the gasket and the flange of the bottle.

24. The container according to claim 20, wherein the valve member is biased towards the closed position by a resilient member.

25. The container according to claim 20, wherein the wall of the bottle comprises metal.

26. The container according to claim 25, wherein the wall of the bottle has an inner surface, the inner surface having a polymer layer applied thereto.

27. An anesthetic container comprising:
    a bottle having a wall defining a receptacle and a neck with a passage in fluid communication with the receptacle;

a valve assembly including a flange with a fluid-tight connection to the bottle; and a ferrule disposed over at least a portion of the flange of the valve assembly and about at least a portion of the neck of the bottle to secure the valve assembly to the bottle and to form a space between the ferrule and the valve assembly or bottle, the valve assembly having at least one vent formed, at least in part, in the flange that permits air trapped in the space between the ferrule and the valve assembly or the bottle to escape.

28. An anesthetic container comprising:

a bottle having a wall defining a receptacle and a neck with a passage in fluid communication with the receptacle;

a valve assembly including a flange with a fluid-tight connection to the bottle; and a ferrule disposed over at least a portion of the flange of the valve assembly and about at least a portion of the neck of the bottle to secure the valve assembly to the bottle and to form a space between the ferrule and the valve assembly or bottle, the bottle having at least one vent formed, at least in part, in the wall of the bottle that permits air trapped in the space between the ferrule and the valve assembly or the bottle to escape.

\* \* \* \* \*

UNITED STATES PATENT AND TRADEMARK OFFICE
CERTIFICATE OF CORRECTION

| | | |
|---|---|---|
| PATENT NO. | : 7,882,970 B2 | Page 1 of 1 |
| APPLICATION NO. | : 12/166986 | |
| DATED | : February 8, 2011 | |
| INVENTOR(S) | : Nathan Mitchell et al. | |

It is certified that error appears in the above-identified patent and that said Letters Patent is hereby corrected as shown below:

On the Title Page:

At Item (73), "Baxter Healthcare Corporation" should be -- Baxter International Inc. --.

Signed and Sealed this
Twenty-seventh Day of March, 2012

David J. Kappos
*Director of the United States Patent and Trademark Office*